United States Patent
Rezania

(10) Patent No.: US 10,519,424 B2
(45) Date of Patent: Dec. 31, 2019

(54) METHODS OF ENHANCING EXPRESSION OF SOMATOSTATIN IN PANCREATIC ENDOCRINE CELLS

(71) Applicant: Janssen Biotech, Inc., Horsham, PA (US)

(72) Inventor: Alireza Rezania, Horsham, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 16/119,862

(22) Filed: Aug. 31, 2018

(65) Prior Publication Data

US 2018/0371420 A1    Dec. 27, 2018

Related U.S. Application Data

(62) Division of application No. 13/911,829, filed on Jun. 6, 2013, now Pat. No. 10,066,210.

(60) Provisional application No. 61/657,160, filed on Jun. 8, 2012.

(51) Int. Cl.
    *C12N 5/071* (2010.01)
(52) U.S. Cl.
    CPC ........ *C12N 5/0676* (2013.01); *C12N 2501/50* (2013.01); *C12N 2501/998* (2013.01); *C12N 2506/02* (2013.01)

(58) Field of Classification Search
    None
    See application file for complete search history.

(56) References Cited

U.S. PATENT DOCUMENTS 10,066,210 B2 * 9/2018 Rezania .............. C12N 5/0676
2007/0154981 A1    7/2007 Hori et al.

FOREIGN PATENT DOCUMENTS

WO    WO 2010/051223 A1    5/2010

OTHER PUBLICATIONS

Sulbacher et al Stem Cell Rev, 2009. pp. 159-173. (Year: 2009).*
D'Amour et al., Production of pancreatic hormone-expressing endocrine cells from human embryonic stem cells, *Nature Biotechnology*, Oct. 19, 2006, 24(11)1392-1401.
Hosoya, et al., Induction of Differentiation of Undifferentiated Cells into Pancreatic Beta-Cells in Vertebrates, *Int. J. Dev. Biol.*, 2012, 56:313-323.

* cited by examiner

*Primary Examiner* — Blaine Lankford
(74) *Attorney, Agent, or Firm* — Klarquist Sparkman, LLP

(57) ABSTRACT

The present invention provides methods to promote differentiation of pancreatic endoderm cells to pancreatic endocrine rich clusters and to enhance insulin expression in hormone-expressing cells.

13 Claims, 10 Drawing Sheets

Control

+ 50 ng/ml Ephrin A3

+100 ng/ml Eprhin A3

Control

+50 ng/ml Ephrin A4

+100 ng/ml Ephrin A4

S6 1D

S6 7D

S6 10D

S6 10D

Hb9

NKX6.1

Insulin

Hb9

S6 3D (10X)

S6 3D (20X)

NKX6.1+
Epithelial cord

Endocrine
clusters

METHODS OF ENHANCING EXPRESSION OF SOMATOSTATIN IN PANCREATIC ENDOCRINE CELLS

CROSS REFERENCE TO RELATED APPLICATION

The present application is a divisional of U.S. Ser. No. 13/911,829, filed Jun. 6, 2013 (now allowed), which claims the benefit of U.S. Provisional Patent Application Ser. No. 61/657,160, filed Jun. 8, 2012, both of which are incorporated herein by reference in their entirety.

FIELD OF THE INVENTION

The present invention is in the field of cell differentiation. More specifically, the invention discloses use of Ephrin ligands and sphingosine-1-phosphate as regulators of differentiation of pluripotent stem cells to endocrine cells.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver, will develop from the endoderm, via an intermediate stage. The intermediate stage in this process is the formation of definitive endoderm. Definitive endoderm cells express a number of markers, such as, HNF3beta, GATA4, MIXL1, CXCR4 and SOX17.

By the end of gastrulation, the endoderm is partitioned into anterior-posterior domains that can be recognized by the expression of a panel of factors that uniquely mark anterior, mid, and posterior regions of the endoderm. For example, Hhex, and Sox2 identify the anterior region while Cdx1, 2, and 4 identify the posterior half of the endoderm.

Migration of endoderm tissue brings the endoderm into close proximity with different mesodermal tissues that help in regionalization of the gut tube. This is accomplished by a plethora of secreted factors, such as FGFs, Wnts, TGF-Bs, retinoic acid (RA), and BMP ligands and their antagonists. For example, FGF4 and BMP promote Cdx2 expression in the presumptive hindgut endoderm and repress expression of the anterior genes Hhex and SOX2 (2000 Development, 127:1563-1567). WNT signaling has also been shown to work in parallel to FGF signaling to promote hindgut development and inhibit foregut fate (2007 Development, 134:2207-2217). Lastly, secreted retinoic acid by mesenchyme regulates the foregut-hindgut boundary (2002 Curr Biol, 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. For example, the regionalized pancreas domain in the gut tube shows a very high expression of PDX1 and very low expression of CDX2 and SOX2. Similarly, the presence of high levels of Foxe1 are indicative of esophagus tissue; highly expressed in the lung tissue is NKX2.1; SOX2/Odd1 (OSR1) are highly expressed in stomach tissue; expression of PROX1/Hhex/AFP is high in liver tissue; SOX17 is highly expressed in biliary structure tissues; PDX1, NKX6.1/PTf1a, and NKX2.2 are highly expressed in pancreatic tissue; and expression of CDX2 is high in intestine tissue. The summary above is adapted from Dev Dyn 2009, 238:29-42 and Annu Rev Cell Dev Biol 2009, 25:221-251.

Formation of the pancreas arises from the differentiation of definitive endoderm into pancreatic endoderm (2009 Annu Rev Cell Dev Biol, 25:221-251; 2009 Dev Dyn, 238:29-42). Dorsal and ventral pancreatic domains arise from the foregut epithelium. Foregut also gives rise to the esophagus, trachea, lungs, thyroid, stomach, liver, pancreas, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

D'Amour et al. describes the production of enriched cultures of human embryonic stem (ES) cell-derived definitive endoderm in the presence of a high concentration of activin and low serum (Nature Biotechnol 2005, 23:1534-1541; U.S. Pat. No. 7,704,738). Transplanting these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent Publication No. 2005/0266554A1). Subsequent transplantation of these pancreatic precursor cells in the fat pad of immune deficient mice resulted in formation of functional pancreatic endocrine cells following a 3-4 month maturation phase (U.S. Pat. Nos. 7,993,920 and 7,534,608).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-B receptor and BMP receptors (Development 2011, 138:861-871; Diabetes 2011, 60:239-247) have been used to significantly enhance number of pancreatic endocrine cells. In addition, small molecule activators have also been used to generate definitive endoderm cells or pancreatic precursor cells (Curr Opin Cell Biol 2009, 21:727-732; Nature Chem Biol 2009, 5:258-265).

Although great strides have been made in improving protocols to generate pancreatic cells from human pluripotent stem cells, there is still a need to generate a protocol that results in functional endocrine cells and in particular beta cells. Here, we demonstrate that a class of Ephrin ligands and sphingosine-1-phosphate or agonists of sphingosine receptor enhance production of endocrine cells and accelerate clustering of endocrine hormones and endocrine precursor cells.

SUMMARY

In an embodiment, the present invention relates to a method of enhancing expression of insulin and NKX6.1 by culturing a population of pancreatic endoderm cells in medium comprising Ephrin A4 or Ephrin A3. In some embodiments, the population of pancreatic endoderm cells do not substantially express CDX2 or SOX2. In some embodiments, the population pancreatic endoderm cells are obtained by a stepwise differentiation of pluripotent cells. In some embodiments, the pluripotent cells are human embryonic pluripotent cells.

In an embodiment, the invention concerns a method of enhancing expression of somatostatin while suppressing the expression of insulin, glucagon, and ghrelin by culturing pancreatic endoderm cells in medium comprising Activin A or Activin C. In some embodiments, the population of pancreatic endoderm cells treated with Activin A or Activin C expresses more somatostatin as a population of pancreatic endoderm cells non-treated with Activin A or Activin C. In some embodiments, the expression of insulin is suppressed in the population of pancreatic endoderm cells treated with Activin A or Activin C as compared to the expression of insulin in a population of pancreatic endoderm cells non-treated with Activin A or Activin C. In some embodiments, the expression of glucagon in the population of pancreatic endoderm cells treated with Activin A or Activin C is suppressed as compared to the expression of glucagon in a population of pancreatic endoderm cells non-treated with Activin A or Activin C. In some embodiments, the expression of ghrelin is suppressed in the population of pancreatic endoderm cells treated with Activin A or Activin C as compared to the expression of ghrelin in a population of pancreatic endoderm cells non-treated with Activin A or Activin C. In some embodiments, the pancreatic endoderm cells do not substantially express CDX2 or SOX2. In some embodiments, the pancreatic endoderm cells treated with Activin A or Activin C are obtained by a stepwise differentiation of pluripotent cells. In some embodiments, the pluripotent cells where the pancreatic endoderm cells are derived from are human embryonic pluripotent cells.

In an embodiment, the invention refers to a method of enhancing expression of NKX6.1 by treating pancreatic endoderm cells in medium comprising semaphorin 3a or Epigen. In some embodiments, the population of pancreatic endoderm cells treated with medium comprising semaphorin 3a or Epigen expresses an enhanced amount of NKX6.1 as compared to pancreatic endoderm cells non-treated with medium comprising semaphorin 3a or Epigen. In some embodiments, the level of expression of hormones such as insulin, glucagon, and gherlin is not affected in pancreatic endoderm cells treated with medium comprising semaphorin 3a or Epigen as compared to pancreatic endoderm cells not treated with medium comprising semaphorin 3a or Epigen. In some embodiments, the pancreatic endoderm cells do not substantially express CDX2 or SOX2. In some embodiments, the pancreatic endoderm cells treated with medium comprising semaphorin 3a or Epigen are obtained by a stepwise differentiation of pluripotent cells. In some embodiments, the pluripotent cells where the pancreatic endoderm cells are derived from are human embryonic pluripotent cells.

In some embodiments, the present invention relates to a stepwise method of differentiating pluripotent cells comprising culturing pancreatic endoderm cells in medium comprising Ephrin A4, Ephrin A3, Activin A, Activin C, semaphorin 3a, or Epigen. In some embodiments, the pancreatic endoderm cells are cultured in medium comprising Ephrin A4 or Ephrin A3. In some embodiments, the pancreatic endoderm cells are cultured in medium comprising Activin A or Activin C. In some embodiments, the pancreatic endoderm cells are cultured in medium comprising semaphorin 3a, or Epigen. In some embodiments, the pluripotent stem cells where the pancreatic endoderm cells are derived from are human embryonic pluripotent stem cells.

In an embodiment, the present invention relates to a method of inducing expression of endocrine clusters by treating pancreatic endocrine cells with sphingosine-1 receptor agonist. In some embodiments, the sphingosine-1 receptor agonist used for treating pancreatic endocrine cells is sphingosine-1-phosphate (S1P)

Also contemplated as embodiments of the invention are cells prepared by the methods of the invention, and methods of using the cells of the invention.

BRIEF DESCRIPTION OF THE DRAWINGS

FIG. 2A, control;

FIG. 2B, cells treated with 50 ng/ml Ephrin-A3; and FIG. 2C, cells treated with 100 ng/ml Ephrin-A3, as described in Example 2.

FIG. 3A, control; FIG. 3B, cells treated with 50 ng/ml Ephrin-A4; and FIG. 3C, cells treated with 100 ng/ml Ephrin-A4, as described in Example 2.

FIG. 6C, control cells; FIG. 6D, cells treated with S1P.

DETAILED DESCRIPTION

Figure 1A:
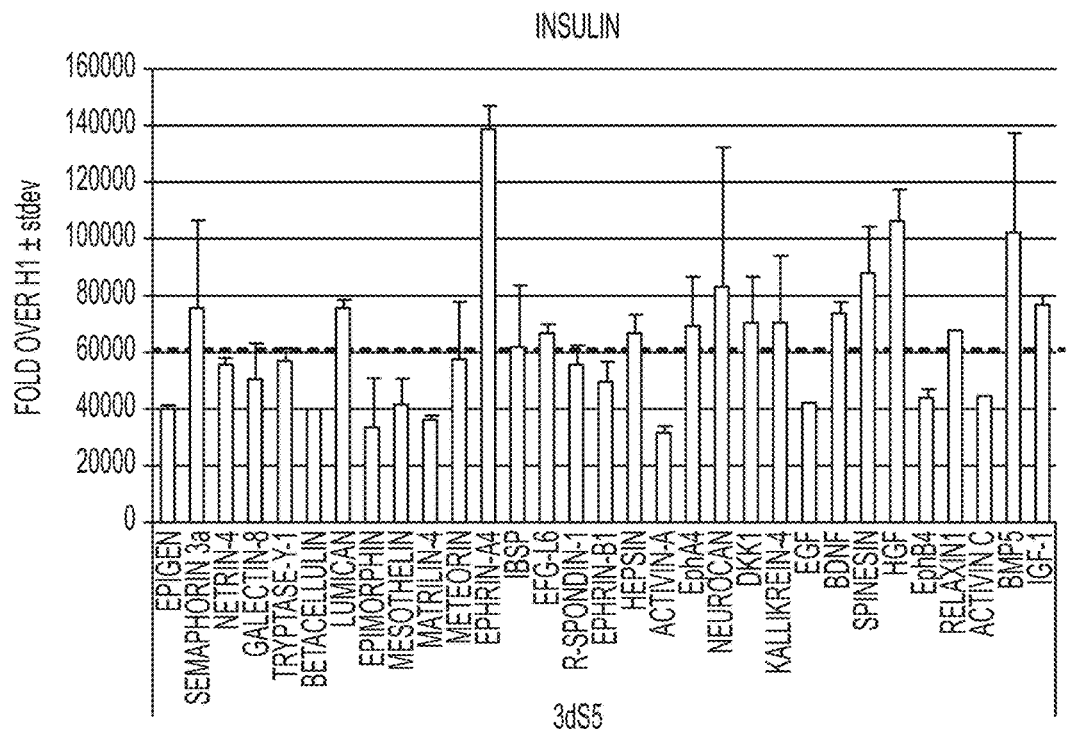
FIG. 1A to FIG. 1G shows data from real-time PCR analyses of the expression of the following genes in cells of the human embryonic stem cell line H1 differentiated as described in Example 1: insulin (FIG. 1A), somatostatin (FIG. 1B), ghrelin (FIG. 1C), glucagon (FIG. 1D), PDX1 (FIG. 1E), NKX6.1 (FIG. 1F), and NGN3 (FIG. 1G).
Figure 1B:
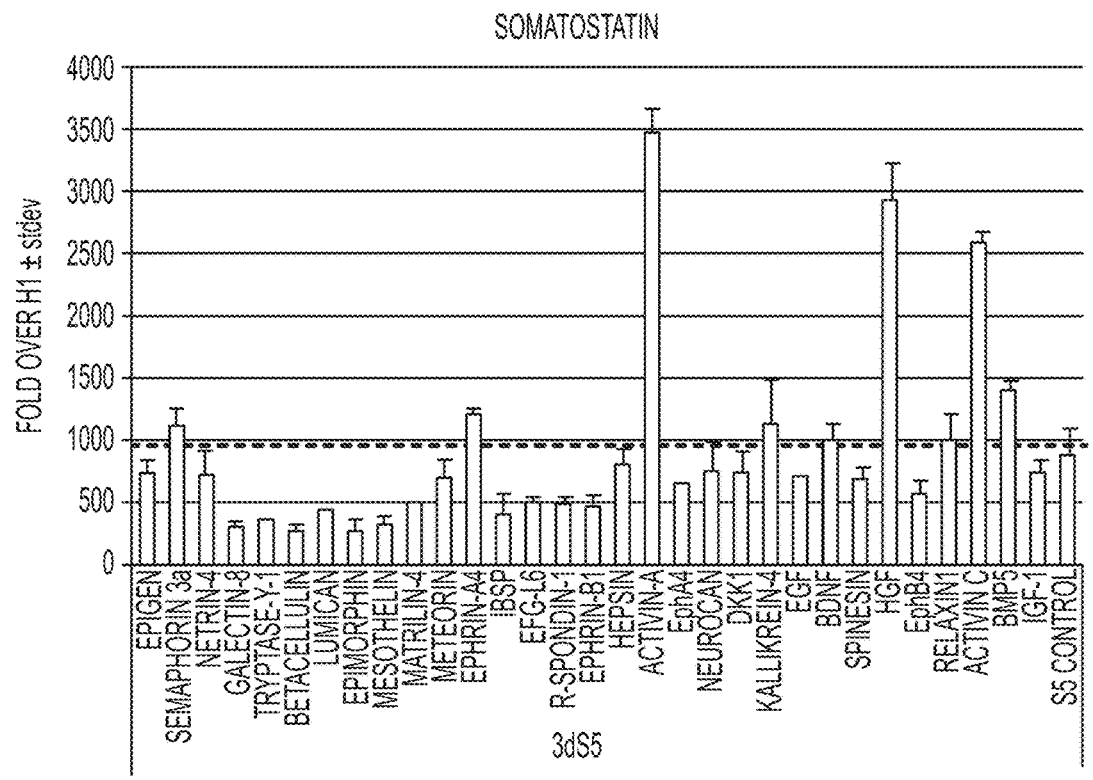
Figure 1C:
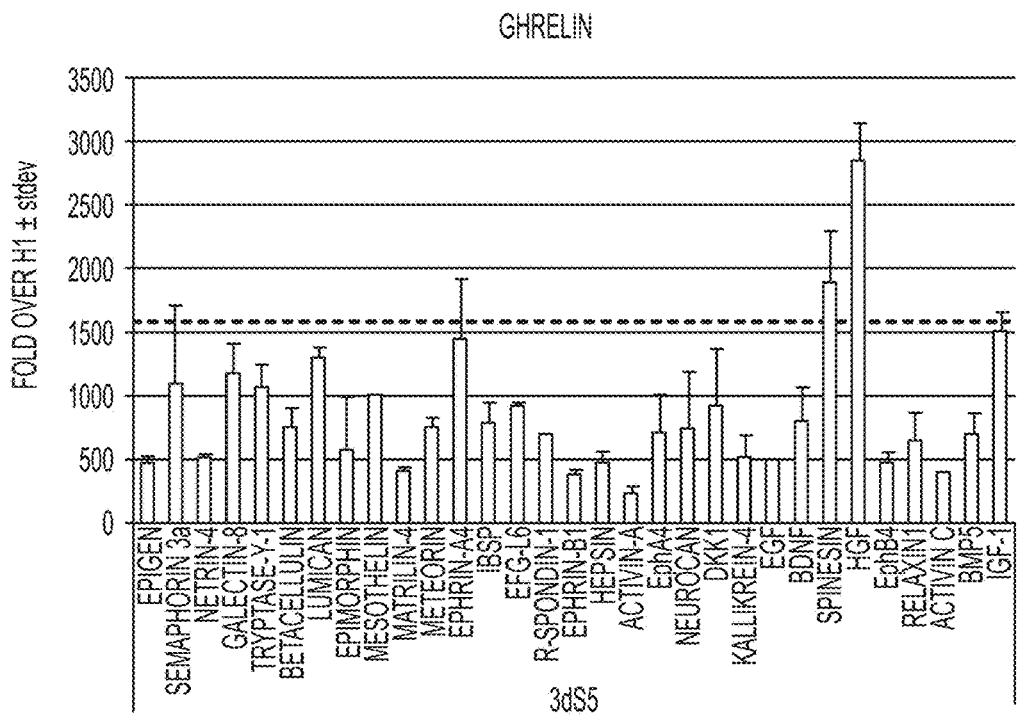
Figure 1D:
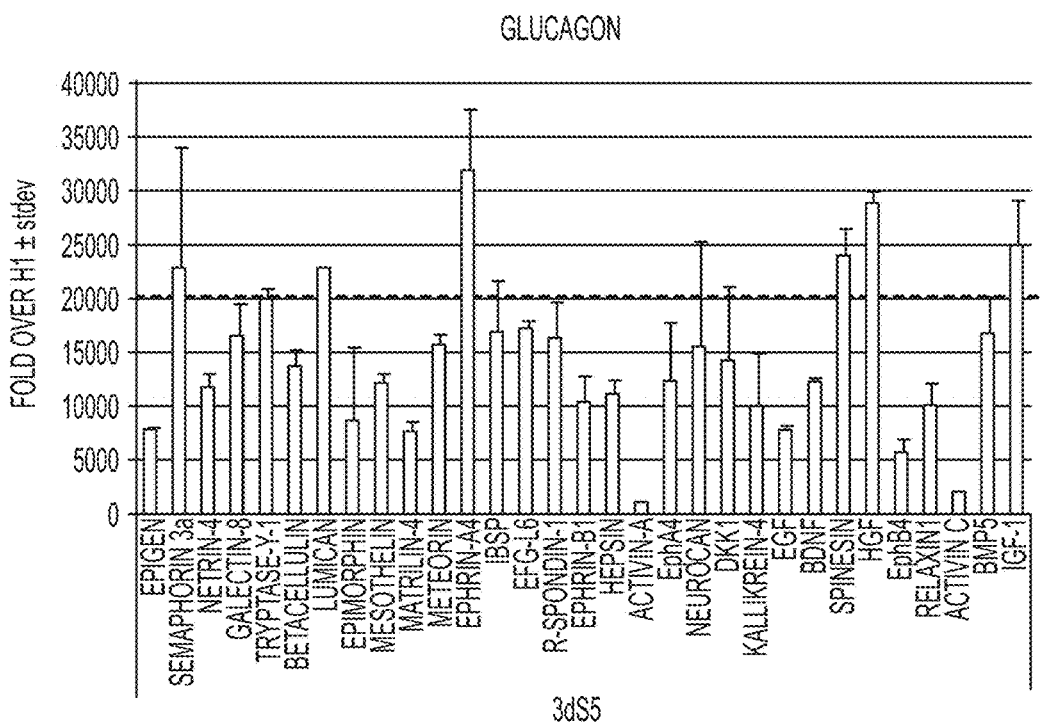
Figure 1E:
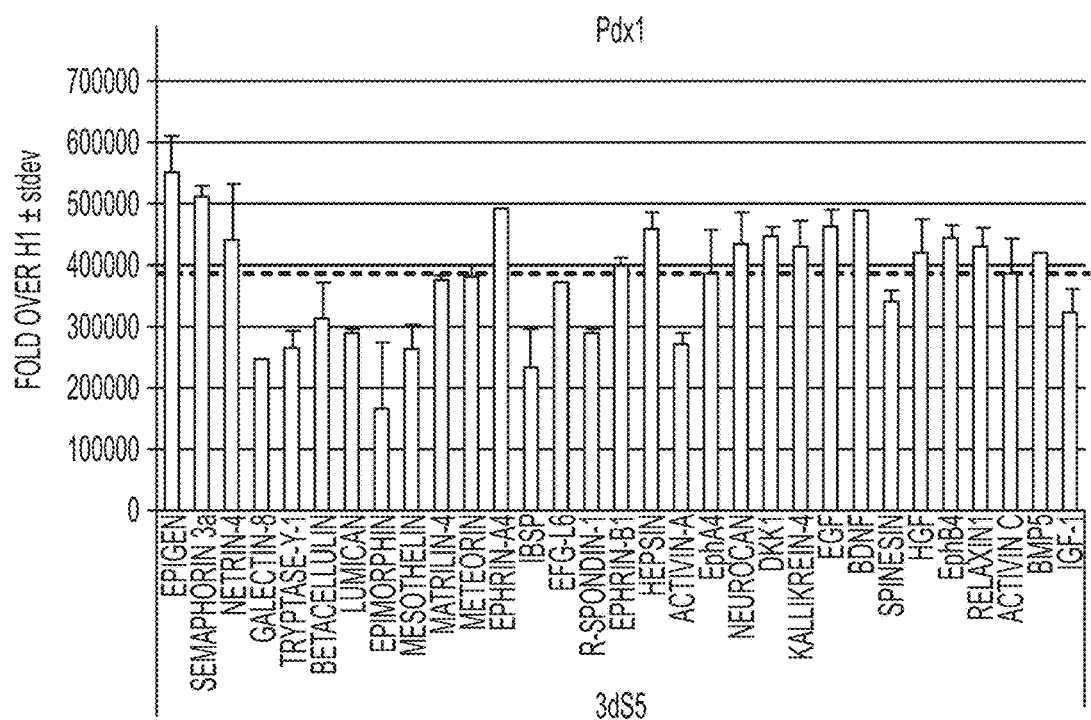
Figure 1F:
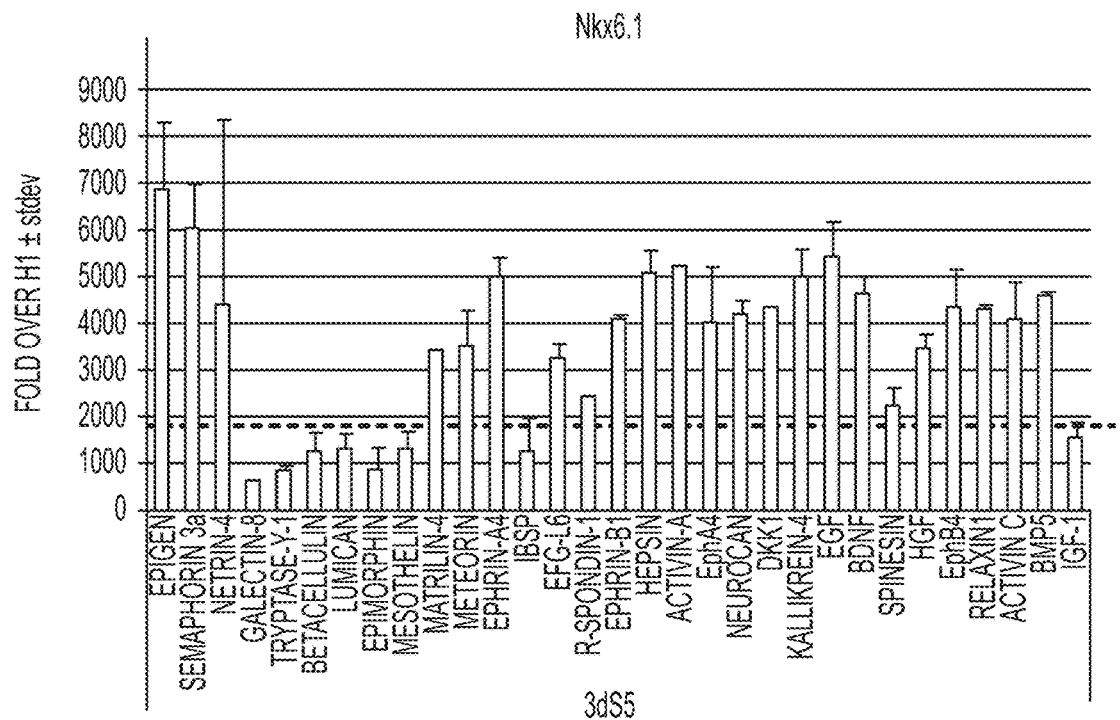

For clarity of disclosure, and not by way of limitation, the detailed description of the invention is divided into the following subsections that describe or illustrate certain features, embodiments or applications of the present invention.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm). Stem cells also give rise to tissues of multiple germ layers following transplantation and contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is detected in the cell. Similarly, the cell is "negative for" a specific marker, or "negative" when the specific marker is not detected in the cell.

As used herein, "Cell density" and "Seeding Density" are used interchangeably herein and refer to the number of cells seeded per unit area of a solid or semisolid planar or curved substrate.

As used herein, "stage 1" and "S1" are used interchangeably to identify cells expressing markers characteristic of the definitive endoderm (DE).

"Definitive endoderm", as used herein, refers to cells which bear the characteristics of cells arising from the epiblast during gastrulation and which form the gastrointestinal tract and its derivatives. Definitive endoderm cells express at least one of the following markers: HNF3 beta, GATA4, SOX17, CXCR4, Cerberus, OTX2, goosecoid, C-Kit, CD99, and MIXL1.

"Gut tube", as used herein, refers to cells derived from definitive endoderm that express at least one of the following markers: HNF3-beta, HNF1-beta, or HNF4-alpha. Gut tube cells can give rise to all endodermal organs, such as lungs, liver, pancreas, stomach, and intestine.

Used herein interchangeably are "stage 2" and "S2" which identify cells expressing markers characteristic of the primitive gut tube.

"Foregut endoderm" refers to endoderm cells that give rise to esophagus, lungs, stomach, liver, pancreas, gall bladder, and a portion of the duodenum.

"Posterior foregut" refers to endoderm cells that can give rise to posterior stomach, pancreas, liver, and a portion of the duodenum.

"Mid-gut endoderm" refers to endoderm cells that can give rise to the intestines, portions of the duodenum, appendix, and ascending colon.

"Hind-gut endoderm" refers to endoderm cells that can give rise to the distal third of the transverse colon, the descending colon, sigmoid colon and rectum.

Both "stage 3" and "S3" are used interchangeably to identify cells expressing markers characteristic of the foregut endoderm. "Cells expressing markers characteristic of the foregut lineage", as used herein, refers to cells expressing at least one of the following markers: PDX1, FOXA2, CDX2, SOX2, and HNF4 alpha.

Used interchangeably herein are "stage 4" and "S4" to identify cells expressing markers characteristic of the pancreatic foregut precursor. "Cells expressing markers characteristic of the pancreatic foregut precursor lineage", as used herein, refers to cells expressing at least one of the following markers: PDX1, NKX6.1, HNF6, FOXA2, PTF1a, Prox1 and HNF4 alpha.

As used herein, "stage 5" and "S5" are used interchangeably to identify cells expressing markers characteristic of the pancreatic endoderm and pancreatic endocrine precursor cells. "Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage do not substantially express CDX2 or SOX2.

"Pancreatic endocrine cell", or "Pancreatic hormone expressing cell", or "Cells expressing markers characteristic of the pancreatic endocrine lineage", or "Stage 6 cells", or "S6 cells" are used interchangeably herein, and refer to a cell capable of expressing at least one of the following hormones: insulin, glucagon, somatostatin, ghrelin, and pancreatic polypeptide.

"Pancreatic insulin positive cell" refers to an endocrine population of cells expressing insulin, HB9, NKX2.2 and NKX6.1.

"Pancreatic endocrine precursor cell" or "Pancreatic endocrine progenitor cell" refers to pancreatic endoderm cells capable of becoming a pancreatic hormone expressing cell. Such a cell can express at least one of the following markers: NGN3, NKX2.2, NeuroD, ISL-1, Pax4, Pax6, or ARX.

Used interchangeably herein are "d1", "d1", and "day 1"; "d2", "d 2", and "day 2"; "d3", "d 3", and "day 3", and so on. These number letter combinations refer to a specific day of incubation in the different stages during the stepwise differentiation protocol of the instant application.

"Glucose" and "D-Glucose" are used interchangeably herein and refer to dextrose, a sugar commonly found in nature.

Used interchangeably herein are "NeuroD" and "NeuroD 1" which identify a protein expressed in pancreatic endocrine progenitor cells and the gene encoding it.

Used interchangeably herein are "LDN" and "LDN-193189" to indicate a BMP receptor inhibitor available from Stemgent, CA, USA.

Isolation, Expansion and Culture of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al. 1998, Science 282:1145-1147). Differentiation of pluripotent stem cells in vitro results in the loss of SSEA-4, Tra-1-60, and Tra-1-81 expression. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, CA, USA). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTesr®1 media (StemCell Technologies, Vancouver, Canada) may be used for routine expansion of the cells. Pluripotent cells may be readily removed from culture plates using enzymatic, mechanical or use of various calcium chelators such as EDTA (Ethylenediaminetetraacetic acid). Alternatively, pluripotent cells may be expanded in suspension in the absence of any matrix proteins or a feeder layer.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, for example the human embryonic stem cell lines H1, H7, and H9 (WiCell Research Institute, Madison, Wis., USA). Also suitable are cells taken from a pluripotent stem cell population already cultured in the absence of feeder cells. Also suitable are inducible pluripotent cells (IPS) or reprogrammed pluripotent cells that can be derived from adult somatic cells using forced expression of a number of pluripotent related transcription factors, such as OCT4, NANOG, Sox2, KLF4, and ZFP42 (Annu Rev Genomics Hum Genet 2011, 12:165-185). The human embryonic stem cells used in the methods of the invention may also be prepared as described by Thomson et al. (U.S. Pat. No. 5,843,780; Science, 1998, 282:1145-1147; Curr Top Dev Biol 1998, 38:133-165; Proc Natl Acad Sci U.S.A. 1995, 92:7844-7848).

Formation of Cells Expressing Markers Characteristic of the Pancreatic Endoderm Lineage from Pluripotent Stem Cells Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX1 and NKX6.1 are substantially higher than the expression of CDX2 and SOX2.

Markers characteristic of the pancreatic endocrine lineage are selected from the group consisting of NGN3, NEUROD, ISL1, PDX1, NKX6.1, PAX4, ARX, NKX2.2, and PAX6. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

The pancreatic endocrine cells of the invention are cells expressing markers characteristic of the β cell lineage. A cell expressing markers characteristic of the β cell lineage expresses PDX1 and at least one of the following transcription factors: NKX2.2, NKX6.1, NEUROD, ISL1, HNF3 beta, MAFA, PAX4, and PAX6. In one aspect of the present invention, a cell expressing markers characteristic of the β cell lineage is a β cell.

In an embodiment, the present invention relates to a method of enhancing expression of insulin and NKX6.1 by culturing a population of stage 5 cells in medium comprising Ephrin A4 or Ephrin A3. In some embodiments, the expression of insulin and NKX6.1 is enhanced in the population of cells to at least 2 times as much as the expression of insulin and NKX6.1 in a population of non-treated cells. In some embodiments, the population of stage 5 cells do not substantially express CDX2 or SOX2. In some embodiments, the population stage 5 cells are obtained by a stepwise differentiation of pluripotent cells. In some embodiments, the pluripotent cells are human embryonic pluripotent cells.

In an embodiment, the invention concerns a method of enhancing expression of somatostatin while suppressing the expression of insulin, glucagon, and ghrelin by culturing stage 5 cells in medium comprising Activin A or Activin C. In some embodiments, the treated population of cells expresses at least two times as much somatostatin as non-treated cultures. In some embodiments, the expression of insulin is suppressed to about half as much as the expression of insulin in non-treated cultures. In some embodiments, the expression of glucagon is suppressed to about 1/10 as much as the expression of glucagon in non-treated cultures. In some embodiments, the expression of ghrelin is suppressed to about 1/3 as much as the expression of ghrelin as in non-treated cultures. In some embodiments, the stage 5 cells do not substantially express CDX2 or SOX2. In some embodiments, the stage 5 cells are obtained by a stepwise differentiation of pluripotent cells. In some embodiments, the pluripotent cells are human embryonic pluripotent cells.

In an embodiment, the invention refers to a method of enhancing expression of NKX6.1 by treating stage 5 cells in medium comprising semaphorin 3a or Epigen. In some embodiments, the treated population of cells expresses at least two times as much NKX6.1 as non-treated cultures. In some embodiments, the level of expression of hormones is not affected in treated cultures as compared to untreated cultures. In some embodiments, the stage 5 cells do not substantially express CDX2 or SOX2. In some embodiments, the stage 5 cells are obtained by a stepwise differ-entiation of pluripotent cells. In some embodiments, the pluripotent cells are human embryonic pluripotent cells.

In some embodiments, the present invention relates to a stepwise method of differentiating pluripotent cells comprising culturing stage 5 cells in medium comprising Ephrin A4, Ephrin A3, Activin A, Activin C, semaphorin 3a, or Epigen. In some embodiments, the stage 5 cells are cultured in medium comprising Ephrin A4 or Ephrin A3. In some embodiments, the stage 5 cells are cultured in medium comprising Activin A or Activin C. In some embodiments, the stage 5 cells are cultured in medium comprising semaphorin 3a, or Epigen. In some embodiments, the pluripotent stem cells are human embryonic pluripotent stem cells.

In an embodiment, the invention relates to a method of inducing insulin expression comprising culturing pancreatic endoderm cells with an Ephrin ligand. In some embodiments, the Ephrin ligand is selected from Ephrin A3 and Ephrin A4. In some embodiments, culturing the pancreatic endoderm cells with an Ephrin ligand enhances expression of insulin and NKX6.1. In some embodiments, culturing the pancreatic endoderm cells with an Ephrin ligand enhances expression of insulin and NKX6.1 in the pancreatic endoderm cells to at least 2 times as much as the expression of insulin and NKX6.1 in non-treated pancreatic endoderm cells. In some embodiments, the pancreatic endoderm cells do not substantially express CDX2 or SOX2. In some embodiments, the pancreatic endoderm cells are obtained by a stepwise differentiation of pluripotent stem cells. In some embodiments, the pluripotent stem cells used in the methods of the invention are human embryonic pluripotent stem cells.

In an embodiment, the invention concerns insulin and NKX6.1-expressing cells prepared by the methods of the invention.

In an embodiment, the invention refers to a method for inducing endocrine cluster formation comprising culturing pancreatic endoderm cells with a sphingosine-1 receptor agonist. In some embodiments, the pancreatic endoderm cells are obtained by a stepwise differentiation of pluripotent stem cells. In some embodiments, the pluripotent stem cells are human embryonic pluripotent stem cells.

Publications cited throughout this document are hereby incorporated by reference in their entirety. The present invention is further illustrated, but not limited, by the following examples.

EXAMPLES

Example 1

Identification of EphrinA4 as a Strong Inducer of Insulin Expression

This example was carried out to understand the role of various proteins on the generation of pancreatic endoderm/endocrine cultures from the differentiation of human ES cells.

Cells of the human embryonic stem cell line H1 (hESC H1, passage 40) were seeded as single cells at $1 \times 10^5$ cells/cm$^2$ on MATRIGEL™ (1:30 dilution; BD Biosciences, NJ)-coated dishes in mTeSR®1 media (StemCell Technologies, Vancouver, Canada) supplemented with 10 μM of Y27632 (Rock inhibitor, Catalog No. Y0503, SigmaAldrich, St. Louis, Mo.). Forty-eight hours post seeding, cultures were washed in incomplete PBS (phosphate buffered saline without Mg or Ca). Cultures were differentiated into pancreatic endoderm/endocrine lineages as follows:

a) Stage 1 (Definitive Endoderm (DE)—3 days): Cells were cultured for one day in stage 1 media: MCDB-131 medium (Catalog No. 10372-019, Invitrogen, Carlsbad, Calif.) supplemented with 0.1% fatty acid-free BSA (Catalog No. 68700, Proliant, Ankeny, Iowa), 0.0012 g/ml sodium bicarbonate (Catalog No. 53187, SigmaAldrich, St. Louis, Mo.), 1× GlutaMax™ (Invitrogen Catalog No. 35050-079), 4.5 mM D-Glucose (SigmaAldrich Catalog No. G8769), 100 ng/ml GDF8 (R&D Systems, Minneapolis, Minn.) and 1 µM MCX compound (a GSK3B inhibitor, 14-Prop-2-en-1-yl-3,5,7,14,17,23,27-heptaazatetracyclo [19.3.1.1~2,6~0.1~8,12~]heptacosa-1(25),2(27),3,5,8(26),9,11,21,23-nonaen-16-one, US Patent Application Publication No. 2010-0015711; incorporated herein by reference in its entirety). Cells were then cultured for additional day in MCDB-131 medium supplemented with 0.1% fatty acid-free BSA, 0.0012 g/ml sodium bicarbonate, 1× GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1× GlutaMax™, 4.5 mM D-Glucose, and 100 ng/ml GDF8, then b) Stage 2 (Primitive gut tube—2 days): Cells were treated for two days with MCDB-131 medium supplemented with 0.1% fatty acid-free BSA; 0.0012 g/ml sodium bicarbonate; 1× GlutaMax™; 4.5 mM D-Glucose; 0.25 mM ascorbic acid (Sigma, St. Louis, Mo.) and 25 ng/ml FGF7 (R & D Systems, Minneapolis, Minn.), then c) Stage 3 (Foregut-2 days): Cells were treated with MCDB-131 medium supplemented with a 1:200 dilution of ITS-X (Invitrogen); 4.5 mM Glucose; 1× GlutaMax™; 0.0017 g/ml sodium bicarbonate; 2% fatty acid-free BSA; 0.25 µM SANT-1 (Sigma, St. Louis, Mo.); 10 ng/ml of Activin-A (R & D Systems); 1 µM retinoic acid (RA; Sigma); 25 ng/ml FGF7; 0.25 mM ascorbic acid; 200 nM TPB (a PKC activator; Catalog No. 565740; EMD Chemicals, Gibstown, N.J.); 10 µM forskolin (FSK, Sigma), and 100 nM LDN (a BMP receptor inhibitor; Catalog No. 04-0019; Stemgent; San Diego, Calif.) for day 1. On day 2, cells were treated with MCDB-131 medium supplemented with a 1:200 dilution of ITS-X; 4.5 mM Glucose; 1× GlutaMax™; 0.0017 g/ml sodium bicarbonate; 2% fatty acid-free BSA; 0.25 µM SANT-1; 10 ng/ml of Activin A; 1 µM RA; 25 ng/ml FGF7; 0.25 mM ascorbic acid, 200 nM TPB, 10 µM forskolin and 10 nM LDN, then d) Stage 4 (Pancreatic foregut precursor—2 days); Cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; and 100 nM TPB for two days, then e) Stage 5 (Pancreatic endoderm/endocrine—3 days): Stage 4 cells were treated with MCDB-131 medium supplemented with a 1:200 dilution of ITS-X; 20 mM Glucose; 1× GlutaMax™; 0.0015 g/ml sodium bicarbonate; 2% fatty acid-free BSA; 0.25 µM SANT-1; 50 nM RA; 10 µM forskolin; 0.25 mM ascorbic acid for three days, with the addition of 100 nM ALk5 inhibitor SD-208 (disclosed in Molecular Pharmacology 2007, 72:152-161) for days 2-3 only.

At day 1 of stage 5, the factors listed in Table I, below, were spiked into the media and upon completion of S5 (day 3 of stage 5) mRNA was collected for PCR analysis of relevant pancreatic endoderm/endocrine genes. As a control, cultures were treated only with the S5 media listed above. Total RNA was extracted with the RNeasy Mini Kit (Qiagen; Valencia, Calif.) and reverse-transcribed using a High Capacity cDNA Reverse Transcription Kit (Applied Biosystems, Foster City, Calif.) according to manufacturer's instructions. cDNA was amplified using Taqman Universal Master Mix and Taqman Gene Expression Assays which were pre-loaded onto custom Taqman Arrays (Applied Biosystems). Data were analyzed using Sequence Detection Software (Applied Biosystems) and normalized to undifferentiated human embryonic stem (hES) cells using the AACt method. All primers were purchased from Applied Biosystems.

TABLE I

List of factors tested at S5 of Example 1

| Protein | Concentration | R & D Systems Catalogue Number |
| --- | --- | --- |
| Epigen | 20 ng/ml | 6629-EP-025 |
| Semaphorin 3a | 50 ng/ml | 1250-S3-025 |
| Netrin 4 | 100 ng/ml | 1254-N4-025 |
| Galectin-8 | 100 ng/ml | 1305-GA-050 |
| Tryptase-Y-1 | 20 ng/ml | 1667-SE-010 |
| BetaCellulin | 20 ng/ml | 261-CE-010 |
| Lumican | 100 ng/ml | 2846-LU-050 |
| Epimorphin | 50 ng/ml | 2936-EP-025 |
| Mesothelin | 50 ng/ml | 3265-MS-050 |
| Matrilin-4 | 100 ng/ml | 3380-MN-050 |
| Meteorin | 50 ng/ml | 3475-MN-025 |
| Ephrin-A4 | 100 ng/ml | 369-EA |
| IBSP | 100 ng/ml | 4014-SP-050 |
| EFG-L6 | 50 ng/ml | 4329-EG-025 |
| R-Spondin-1 | 100 ng/ml | 4645-RS-025 |
| Ephrin-B1 | 100 ng/ml | 473-EB-200 |
| Hepsin | 50 ng/ml | 4776-SE-010 |
| Activin A | 20 ng/ml | 338-AC-010 |
| EphA4 | 50 ng/ml | 6827-A4-050 |
| Neurocan | 100 ng/ml | 6508-NC-050 |
| DKK1 | 100 ng/ml | 5439-DK-010 |
| Kallikrein-4 | 50 ng/ml | 1719-SE-010 |
| EGF | 20 ng/ml | 236-EG-200 |
| BDNF | 20 ng/ml | 248-BD-005 |
| Spinesin | 50 ng/ml | 2495-SE-010 |
| HGF | 20 ng/ml | 294-HG-005 |
| EphB4 | 50 ng/ml | 3038-B4-100 |
| Relaxin1 | 50 ng/ml | 3257-RN-025 |
| Activin C | 20 ng/ml | 4879-AC-010 |
| BMP5 | 20 ng/ml | 615-BMC-020 |
| IGF-1 | 20 ng/ml | 291-G1-200 |

Figure 1G:
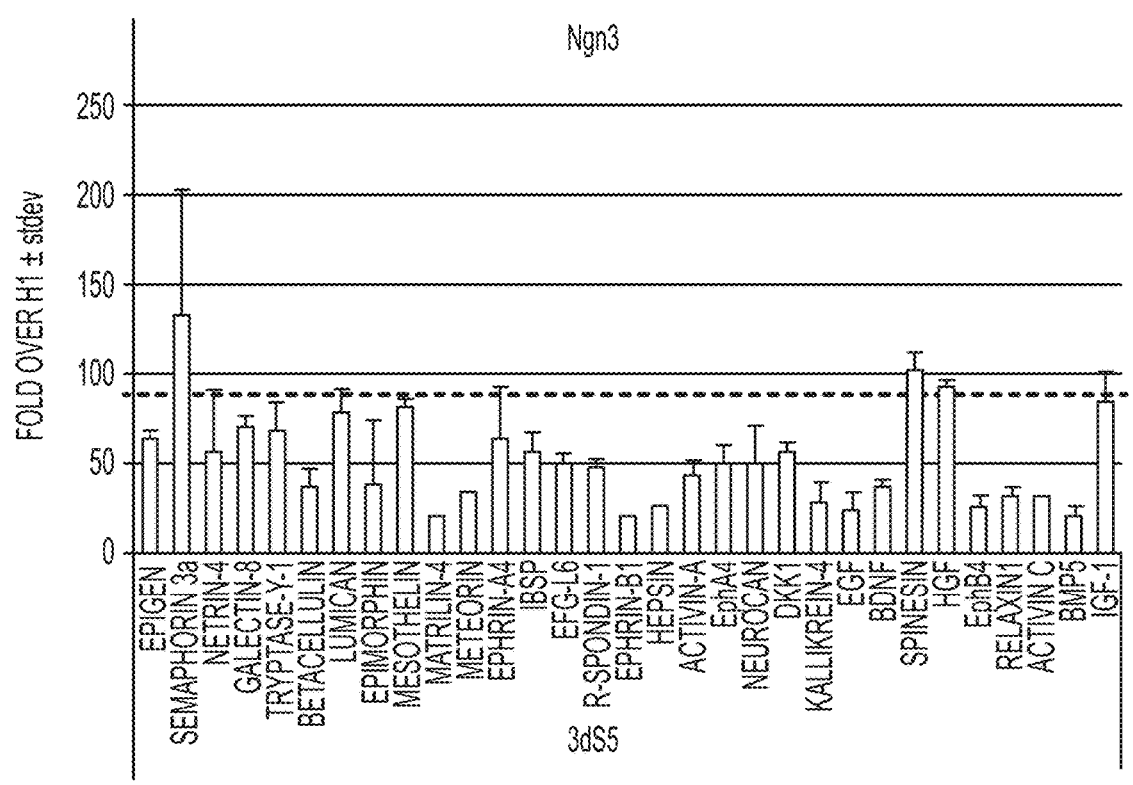

FIG. 1A to FIG. 1G depict data from real-time PCR analyses of the expression of the following genes in cells of the human embryonic stem cell line H1 differentiated to stage 5 as outlined in Example 1 and in the presence of factors listed in Table I: Insulin (FIG. 1A), somatostatin (FIG. 1B), ghrelin (FIG. 1C), glucagon (FIG. 1D), PDX1 (FIG. 1E), NKX6.1 (FIG. 1F), and NGN3 (FIG. 1G).

As shown in FIG. 1, Ephrin-A4 enhanced mRNA expression of NKX6.1 and insulin as compared to control cultures (FIG. 1F) while showing minimal impact on PDX1 (FIG. 1E) and NGN3 expression (FIG. 1G). Factors such as Activin-A and Activin-C significantly enhanced expression of somatostatin (FIG. 1B) while suppressing the expression of insulin (FIG. 1A), glucagon (FIG. 1D), and ghrelin (FIG. 1C). Moreover, factors such as semaphorin 3a and Epigen enhanced NKX6.1 expression while not affecting expression of hormones as compared to untreated cultures. In FIG. 1A to FIG. 1G, the average level of expression of the different markers in control cultures are shown by a dotted line on the graphs.

Example 2

Verification of the Effect of Ephrins on Insulin Expression at S5

This example describes the validation of hits identified in Example 1. In particular, the effect of addition of Ephrin-A3 or Ephrin-A4 at S5 in the protocol listed below.

Cells of the human embryonic stem cell line H1 (hESC H1, passage 40) were seeded as single cells at $1\times10^5$ cells/cm$^2$ on MATRIGEL™ (1:30 dilution; BD Biosciences, NJ)-coated dishes in mTeSR®1 media supplemented with 10 µM of Y27632. Forty-eight hours post seeding, cultures were washed in incomplete PBS (phosphate buffered saline without Mg or Ca). Cultures were differentiated into pancreatic endoderm/endocrine lineages as follows:
- a) Stage 1 (Definitive Endoderm (DE)—3 days): Cells were cultured for one day in stage 1 media (see Example 1, above). Cells were then cultured for an additional day in MCDB-131 medium supplemented with 0.1% fatty acid-free BSA, 0.0012 g/ml sodium bicarbonate, 1× GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1× GlutaMax™, 4.5 mM D-Glucose, and 100 ng/ml GDF8, then
- b) Stage 2 (Primitive gut tube—2 days): Cells were treated for two days with MCDB-131 medium supplemented with 0.1% fatty acid-free BSA; 0.0012 g/ml sodium bicarbonate; 1× GlutaMax™; 4.5 mM D-Glucose; 0.25 mM ascorbic acid (Sigma, MO) and 25 ng/ml FGF7 (R & D Systems, MN), then
- c) Stage 3 (Foregut-2 days): Cells were treated with MCDB-131 medium supplemented with a 1:200 dilution of ITS-X (Invitrogen, Ca); 4.5 mM Glucose; 1× GlutaMax™; 0.0017 g/ml sodium bicarbonate; 2% fatty acid-free BSA; 0.25 µM SANT-1 (Sigma, MO); 10 ng/ml of Activin-A (R& D Systems, MN); 1 µM RA (Sigma, MO); 25 ng/ml FGF7; 0.25 mM ascorbic acid; 200 nM TPB (PKC activator; Catalog No. 565740; EMD Chemicals, Gibstown, N.J.); 10 µM forskolin and 100 nM LDN (BMP receptor inhibitor; Catalog No. 04-0019; Stemgent) for day 1. On day 2, cells were treated with MCDB-131 medium supplemented with a 1:200 dilution of ITS-X; 4.5 mM Glucose; 1× GlutaMax™; 0.0017 g/ml sodium bicarbonate; 2% fatty acid-free BSA; 0.25 µM SANT-1; 10 ng/ml of Activin-A; 1 µM RA; 25 ng/ml FGF7; 0.25 mM ascorbic acid, 200 nM TPB, 10 µM forskolin and 10 nM LDN, then
- d) Stage 4 (Pancreatic foregut precursor—2 days): Cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; and 100 nM TPB for two days, then
- e) Stage 5 (Pancreatic endoderm/endocrine—3 days): Stage 4 cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 10 µM forskolin; 0.25 mM ascorbic acid; 100 nM ALk5 inhibitor (for days 2-3 only) (SD-208, disclosed in Molecular Pharmacology 2007, 72:152-161) and +/−0-100 ng/ml of Ephrin-A3 or Ephrin-A4 (R & D systems, MN) for three days.

Figure 2A:
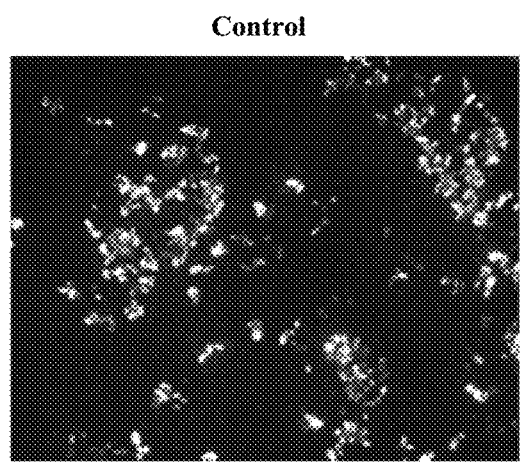
FIG. 2A to FIG. 2C show images of cells immune stained for insulin.
Figure 2B:
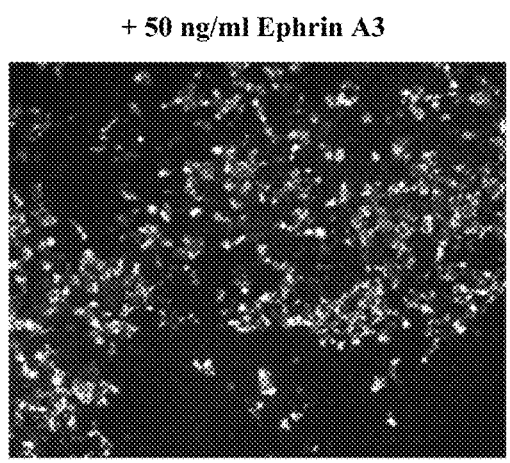
Figure 2C:
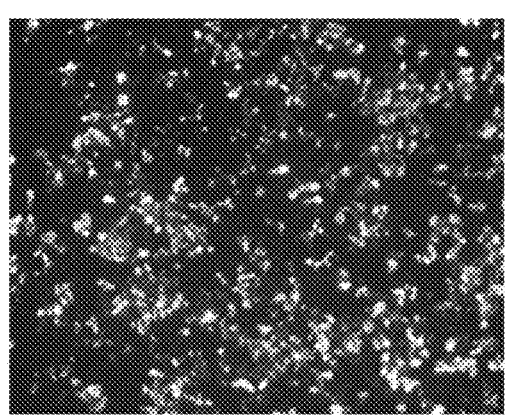
Figure 3A:
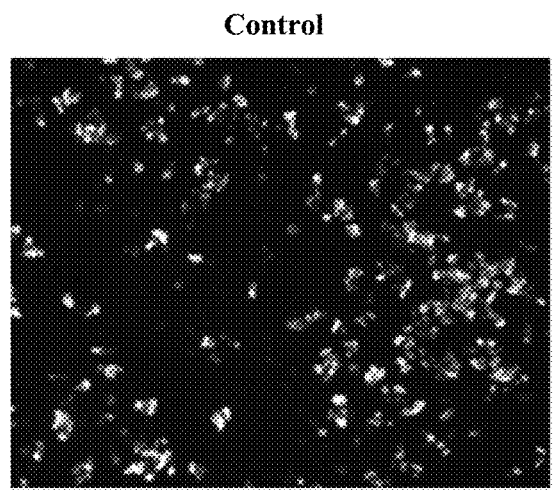
FIG. 3A to FIG. 3C show images of cells immune stained for insulin.
Figure 3B:
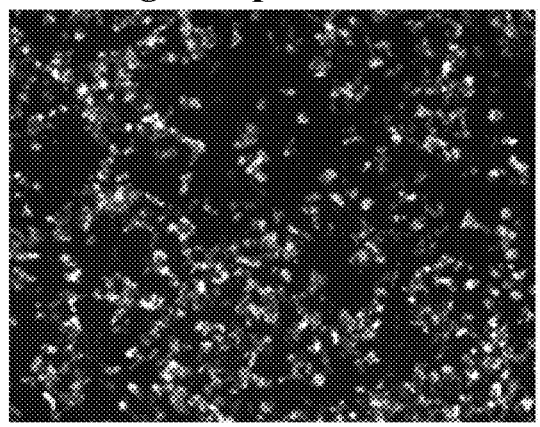
Figure 3C:
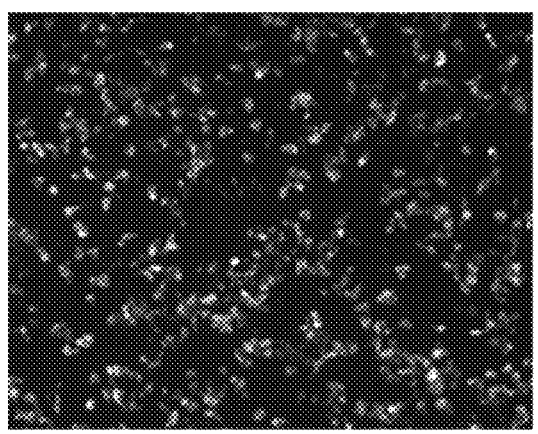

At the end of Stage 5, control and Ephrin-treated cultures were fixed and stained for insulin protein expression (using Guinea Pig anti-insulin antibody from Millipore; Cambridge, Mass.). FIG. 2A to FIG. 2C depic images of cells immunostained for insulin. FIG. 2A, control cells; FIG. 2B, cells treated with 50 ng/ml Ephrin A3; FIG. 2C cells treated with 100 ng/ml Ephrin A3. FIG. 3A to FIG. 3C depicts images of cells immunostained for insulin. FIG. 3A control cells; FIG. 3B, cells treated with 50 ng/ml Ephrin A4; FIG. 3C cells treated with 100 ng/ml Ephrin A4. These data show that, consistent with data from Example 1, addition of both Ephrin-A3 and Ephrin-A4 at stage 5 significantly enhanced protein expression of insulin.

Example 3

Addition of Sphingoisne-1-Phosphate at S6 Significantly Accelerates Formation of Cell Clusters Containing Endocrine Hormones This example describes the progression of endocrine cluster formation at stage 6 and the effect of sphingosine-1-phosphate in accelerating the formation of the endocrine rich clusters.

Cells of the human embryonic stem cell line H1 (hESC H1, passage 40) were seeded as single cells at $1\times10^5$ cells/cm$^2$ on MATRIGEL™ (1:30 dilution; BD Biosciences, NJ) coated dishes in mTeSR®1 media (StemCell Technologies, Vancouver, Canada) supplemented with 10 µM of Y27632. Forty-eight hours post seeding, cultures were washed in incomplete PBS (phosphate buffered saline without Mg or Ca). Cultures were differentiated into pancreatic endoderm/endocrine lineages as follows:
- a) Stage 1 (Definitive Endoderm (DE)—3 days): Cells were cultured for one day in stage 1 media (see Example 1, above). Cells were then cultured for an additional day in MCDB-131 medium supplemented with 0.1% fatty acid-free BSA, 0.0012 g/ml sodium bicarbonate, 1× GlutaMax™, 4.5 mM D-Glucose, 100 ng/ml GDF8, and 0.1 µM MCX compound. Cells were then cultured for an additional day in MCDB-131 medium supplemented with 0.1% fatty acid-free BSA, 0.0012 g/ml sodium bicarbonate, 1× GlutaMax™, 4.5 mM D-Glucose, and 100 ng/ml GDF8, then
- b) Stage 2 (Primitive gut tube—2 days): Cells were treated for two days with MCDB-131 medium supplemented with 0.1% fatty acid-free BSA; 0.0012 g/ml sodium bicarbonate; 1× GlutaMax™; 4.5 mM D-Glucose; 0.25 mM ascorbic acid (Sigma, MO) and 25 ng/ml FGF7 (R & D Systems, MN), then
- c) Stage 3 (Foregut-2 days): Cells were treated with MCDB-131 medium supplemented with a 1:200 dilution of ITS-X (Invitrogen, Ca); 4.5 mM Glucose; 1× GlutaMax™; 0.0017 g/ml sodium bicarbonate; 2% fatty acid-free BSA; 0.25 µM SANT-1 (Sigma, MO); 10 ng/ml of Activin-A (R& D Systems, MN); 1 µM RA (Sigma, MO); 25 ng/ml FGF7; 0.25 mM ascorbic acid; 200 nM TPB (PKC activator; Catalog No. 565740; EMD Chemicals, Gibstown, N.J.); 10 µM forskolin (FSK, Sigma, MO), and 100 nM LDN (BMP receptor inhibitor; Catalog No. 04-0019; Stemgent, CA) for day 1. On day 2, cells were treated with MCDB-131 medium supplemented with a 1:200 dilution of ITS-X;

4.5 mM Glucose; 1× GlutaMax™; 0.0017 g/ml sodium bicarbonate; 2% fatty acid-free BSA; 0.25 µM SANT-1; 10 ng/ml of Activin-A; 1 µM RA; 25 ng/ml FGF7; 0.25 mM ascorbic acid, 200 nM TPB, and 10 nM LDN, then d) Stage 4 (Pancreatic foregut precursor—2 days); Cells were treated with MCDB-131 medium supplemented with a 1:200 dilution of ITS-X; 4.5 mM Glucose; 1× GlutaMax™; 0.0015 g/ml sodium bicarbonate; 2% fatty acid-free BSA; 0.25 µM SANT-1; 50 nM RA; 50 nM LDN-193189; 10 µM forskolin; 0.25 mM ascorbic acid; 2 ng/ml FGF7; 1 ng/ml AA; and 100 nM TPB for two days, then e) Stage 5 (Pancreatic endoderm/endocrine—3 days): Stage 4 cells were treated with MCDB-131 medium supplemented with a 1:200 dilution of ITS-X; 15 mM Glucose; 1× GlutaMax™; 0.0015 g/ml sodium bicarbonate; 2% fatty acid-free BSA; 0.25 µM SANT-1; 50 nM RA; 10 µM forskolin; 0.25 mM ascorbic acid; and 1 ng/ml FGF7 for three days; with the addition of 100 nM ALK5 inhibitor SD-208 at days 2-3 only, then f) Stage 6 (Pancreatic endocrine—3-10 days): Stage 5 cells were treated with MCDB-131 medium supplemented with a 1:200 dilution of ITS-X; 15 mM Glucose; 1× GlutaMax™; 0.0015 g/ml sodium bicarbonate; 2% fatty acid-free BSA; 0.25 µM SANT-1; 50 nM RA; 0.25 mM ascorbic acid; for 3-10 days. In some cultures 10 µM of Sphingosine-1-phosphate (Sigma, MO) was added for three days.

Figure 4A:
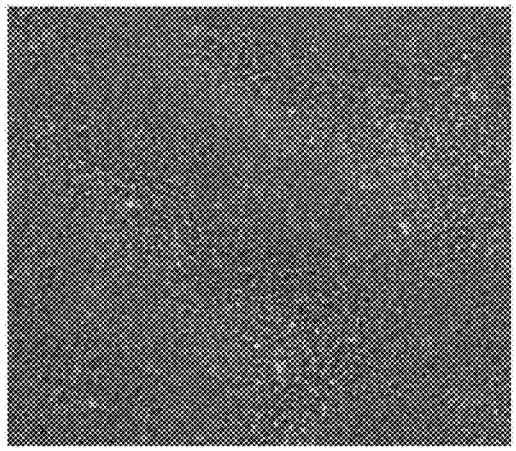
FIG. 4A to FIG. 4D depict phase contrast images of S6 cultures of cells treated with sphingosine-1-phosphate (S1P) and imaged on day 1 (FIG. 4A), day 7 (FIG. 4B), and two different magnifications at day 10 (FIG. 4C and FIG. 4D). The images show that on day 7, there was clear evidence of clustering of endocrine cells and on day 10 the clusters were separated from each other by a thin layer of pancreatic endoderm epithelium.
Figure 4B:
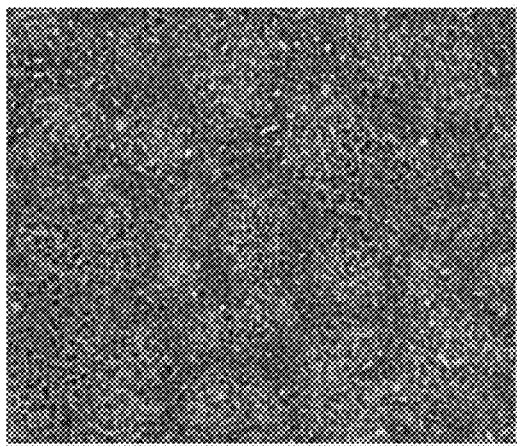
Figure 4C:
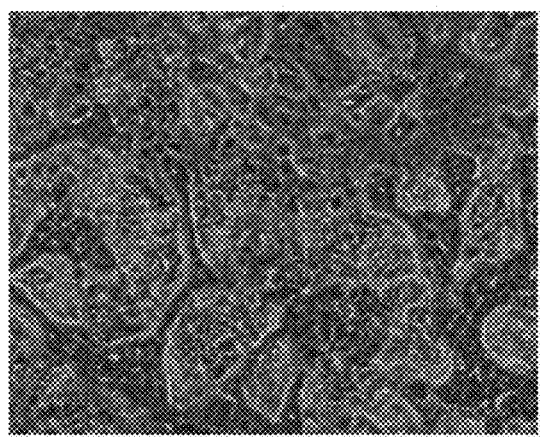
Figure 4D:
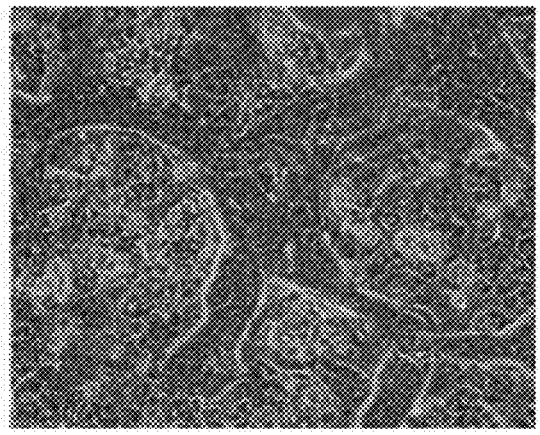

FIG. 4A to FIG. 4D depict phase contrast images of S6 cultures of cells treated with sphingosine-1-phosphate (S1P) and imaged on day 1 (FIG. 4A), day 7 (FIG. 4B), and at two different magnifications at day 10 (FIG. 4C and FIG. 4D). The images show that on day 7, there was clear evidence of clustering of endocrine cells and on day 10 the clusters were separated from each other by a thin layer of pancreatic endoderm epithelium.

Figure 5A:
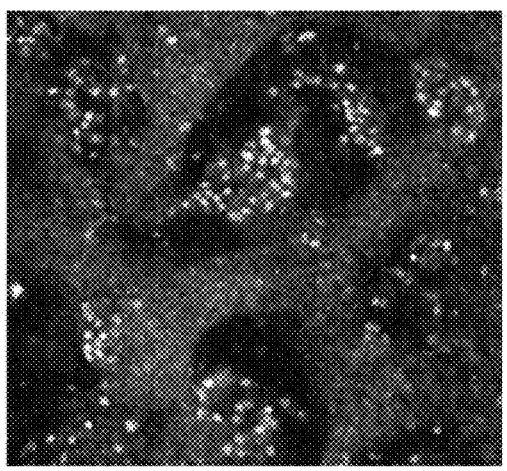
FIG. 5A to FIG. 5D depict images of cells treated with S1P and immunostained for Hb9 (FIG. 5A) and NKX6.1 (FIG. 5B), or immunostained for insulin (FIG. 5C) and Hb9 (FIG. 5D).
Figure 5B:
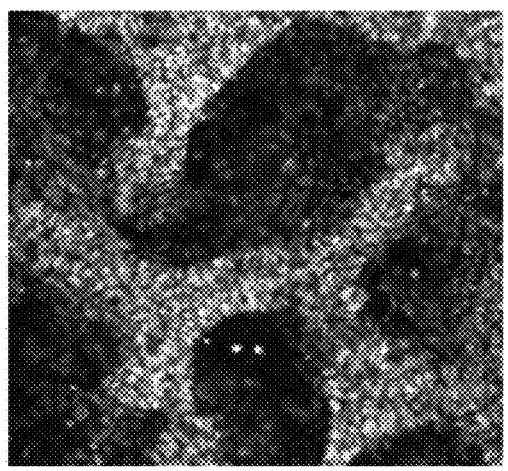
Figure 5C:
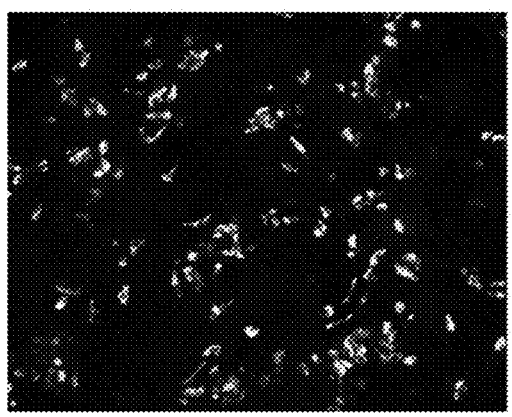
Figure 5D:
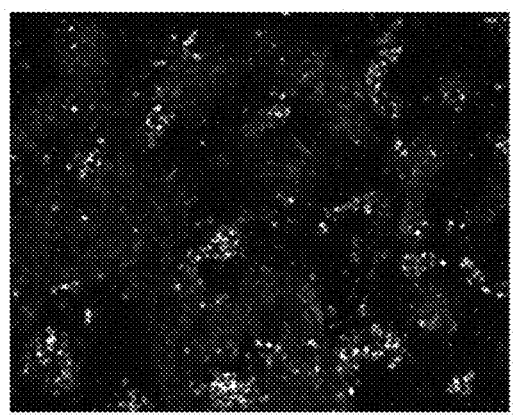

FIG. 5A to FIG. 5D depict images of cells immunostained for Hb9 (FIG. 5A) and NKX6.1 (FIG. 5B), or immunostained for insulin (FIG. 5C) and Hb9 (FIG. 5D). FIG. 5A and FIG. 5B show that the endocrine clusters were enriched for Hb9 while the pancreatic epithelium surrounding the clusters were enriched for NKX6.1. Some of the cells in the Hb9-enriched clusters were also positive for NKX6.1. The clusters were enriched for insulin and Hb9 as shown in FIG. 5C and FIG. 5D. This morphological change closely resembles pancreatic development where NKX6.1+ PDX1+ rich epithelium gives rise to endocrine clusters. In each instance, the pair of images was obtained using different filters from the same field of cells.

Figure 6A:
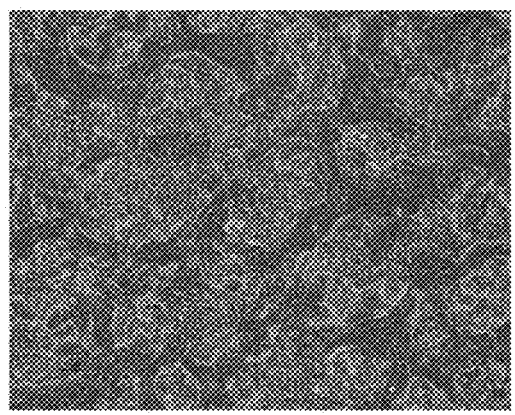
FIG. 6A and FIG. 6B depict phase contrast images, at different magnifications, of cells treated with 10 µM S1P and harvested three days after start of stage 6.
Figure 6B:
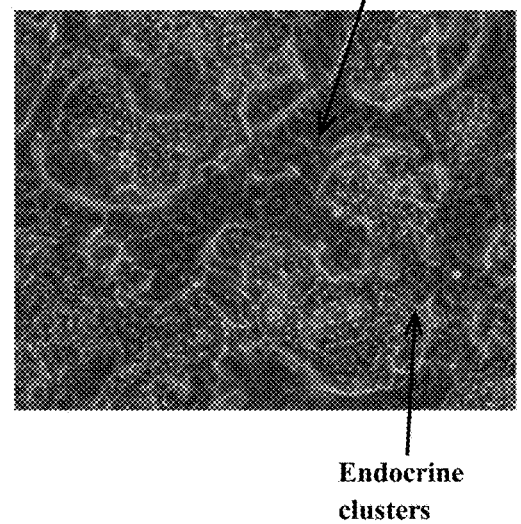

FIG. 6A and FIG. 6B depict phase contrast images, at different magnifications, of cells treated with 10 µM sphingosine-1-phosphate (S1P) and harvested three days after start of stage 6. These images show that endocrine clusters emerged only 3 days after start of stage 6. This is about 7 days earlier than formation of the clusters in control cultures.

Figure 6C:
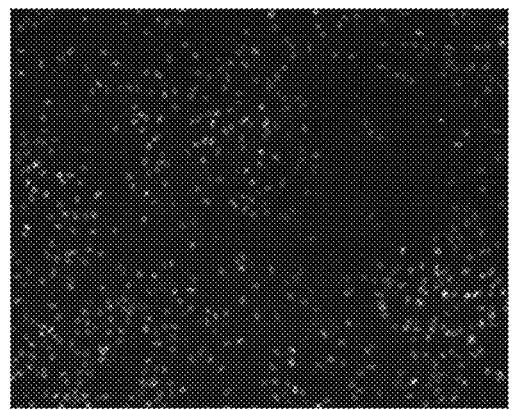
FIG. 6C and FIG. 6D depict images of cells immunostained for NKX2.2.
Figure 6D:
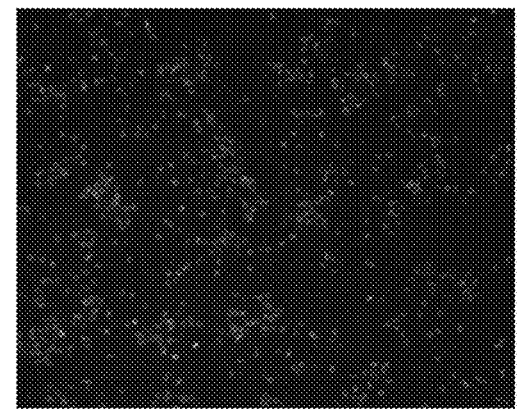

FIG. 6C and FIG. 6D depict images of control cells (FIG. 6C) and cells treated with S1P (FIG. 6D) immunostained for NKX2.2. In S1P-treated cultures, the endocrine clusters were also enriched for NKX2.2+ cells (FIG. 6C), as compared to control cultures where NKX2.2+ cells were distributed uniformly across the culture (FIG. 6D).

What is claimed is:

1. A method of enhancing expression of somatostatin in pancreatic endocrine cells, comprising culturing pancreatic endoderm cells in medium comprising Activin A or Activin C, thereby generating pancreatic endocrine cells having enhanced expression of somatostatin.

2. The method of claim 1, wherein expression of insulin, glucagon, and ghrelin is suppressed in the pancreatic endocrine cells.

3. The method of claim 1, wherein the pancreatic endocrine cells expresses more somatostatin compared to pancreatic endocrine cells generated from pancreatic endoderm cells non-treated with Activin A or Activin C.

4. The method of claim 1, wherein expression of insulin is suppressed in the pancreatic endocrine cells generated from the pancreatic endoderm cells cultured with Activin A or Activin C as compared to expression of insulin in pancreatic endocrine cells generated from pancreatic endoderm cells non-treated with Activin A or Activin C.

5. The method of claim 1, wherein expression of glucagon is suppressed in the pancreatic endocrine cells generated from the pancreatic endoderm cells cultured with Activin A or Activin C as compared to expression of glucagon the pancreatic endocrine cells generated from pancreatic endoderm cells non-treated with Activin A or Activin C.

6. The method of claim 1, wherein expression of ghrelin is suppressed in the pancreatic endocrine cells generated from the pancreatic endoderm cells cultured with Activin A or Activin C as compared to expression of ghrelin in the pancreatic endocrine cells generated from pancreatic endoderm cells non-treated with Activin A or Activin C.

7. The method of claim 1, wherein the pancreatic endoderm cells do not substantially express CDX2 or SOX2.

8. The method of claim 7, wherein the pancreatic endoderm cells cultured with Activin A or Activin C are obtained by a stepwise differentiation of pluripotent cells.

9. The method of claim 8, wherein the pluripotent cells are derived from human embryonic pluripotent cells.

10. The method of claim 1, wherein the pancreatic endoderm cells are human pancreatic endoderm cells.

11. The method of claim 1, wherein the method comprises culturing pancreatic endoderm cells in medium comprising Activin A.

12. The method of claim 1, wherein the method comprises culturing pancreatic endoderm cells in medium comprising Activin C.

13. The method of claim 1, wherein the method further comprises:
  differentiating pluripotent stem cells into definitive endoderm cells;
  differentiating the definitive endoderm cells into primitive guttube cells;
  differentiating the primitive gut tube cells into foregut cells;
  differentiating the foregut cells into pancreatic foregut precursor cells; and
  differentiating the foregut precursor cells into the pancreatic endoderm cells.

* * * * *